United States Patent
Park et al.

[11] Patent Number: 6,159,187
[45] Date of Patent: *Dec. 12, 2000

[54] REINFORCED CATHETER WITH A FORMABLE DISTAL TIP

[75] Inventors: Peter K. Park, Santa Clara; Henry Nita, Milpitas, both of Calif.

[73] Assignee: Target Therapeutics, Inc., Fremont, Calif.

[*] Notice: Under 35 U.S.C. 154(b), the term of this patent shall be extended for 166 days.

[21] Appl. No.: 08/761,659

[22] Filed: Dec. 6, 1996

[51] Int. Cl.[7] .............................. A61M 5/00; A61M 25/00

[52] U.S. Cl. ...................... 604/264; 604/523; 604/530; 604/531

[58] Field of Search ................................ 604/264, 280.2, 604/265, 95, 523, 530, 531

[56] References Cited

U.S. PATENT DOCUMENTS

| | | |
|---|---|---|
| 243,396 | 6/1881 | Pfarre . |
| 2,211,975 | 8/1940 | Hendrickson . |
| 2,437,542 | 3/1948 | Krippendorf . |
| 3,174,851 | 3/1965 | Buehler et al. . |
| 3,351,463 | 11/1967 | Rozner et al. . |
| 3,416,531 | 12/1968 | Edwards . |
| 3,753,700 | 8/1973 | Harrison et al. . |
| 3,757,768 | 9/1973 | Kline . |
| 3,924,632 | 12/1975 | Cook . |
| 4,425,919 | 1/1984 | Alston, Jr. et al. . |
| 4,430,083 | 2/1984 | Ganz et al. . |
| 4,484,586 | 11/1984 | McMickle et al. . |
| 4,516,972 | 5/1985 | Samson . |
| 4,657,024 | 4/1987 | Coneys . |
| 4,676,229 | 6/1987 | Krasnicki et al. . |
| 4,737,153 | 4/1988 | Shimamura et al. . |
| 4,739,768 | 4/1988 | Engelson . |
| 4,806,182 | 2/1989 | Rydell et al. . |
| 4,817,613 | 4/1989 | Jaraczewski et al. . |
| 4,832,681 | 5/1989 | Lenck . |
| 4,898,591 | 2/1990 | Jang et al. . |
| 4,899,787 | 2/1990 | Ouchi et al. . |
| 4,981,478 | 1/1991 | Evard et al. . |
| 5,019,040 | 5/1991 | Itaoka et al. . |
| 5,037,404 | 8/1991 | Gold et al. . |

(List continued on next page.)

FOREIGN PATENT DOCUMENTS

| | | |
|---|---|---|
| 0098100 | 1/1984 | European Pat. Off. . |
| 2 613281 | 10/1988 | France . |
| 3642107 | 6/1987 | Germany . |
| 2-283346 | 11/1990 | Japan . |
| 3-23830 | 1/1991 | Japan . |
| 5-56910 | 3/1993 | Japan . |
| 5-220225 | 8/1993 | Japan . |
| WO 92/057507 | 5/1992 | WIPO . |
| WO 93/05842 | 4/1993 | WIPO . |
| WO 93/15785 | 8/1993 | WIPO . |

*Primary Examiner*—Wynn Wood Coggins
*Assistant Examiner*—LoAn H. Thanh
*Attorney, Agent, or Firm*—Morrison & Foerster LLP

[57] ABSTRACT

This is a section of a catheter which self-forms a selected shape upon application of a modest amount of heat and retains that shape upon cooling and, indeed, upon any reheating. The catheter section includes in its wall a forming member which typically comprises a super-elastic alloy oven braid or at least one coil. The forming member may include other materials and components in addition to the super-elastic element of the forming member. The forming member is typically covered by at least an outer polymeric covering which holds the forming member in a first shape prior to the heating step. Upon softening of the outer layer during that heating step, the forming member self-forms into the desired second shape. The catheter section may be used either in its first shape or its second shape or in any transitional shape between the two. Often the inner lumen of the forming member may contain a second polymeric tubing member. The inner polymeric tubing member is often lubricious. The catheter sections made according to this invention may be used alone or in conjunction with other catheter sections. The more proximal sections of a catheter assembly using this concept are often substantially stiffer.

17 Claims, 5 Drawing Sheets

U.S. PATENT DOCUMENTS

| | | |
|---|---|---|
| 5,057,092 | 10/1991 | Webster, Jr. . |
| 5,069,674 | 12/1991 | Fearnot et al. . |
| 5,176,660 | 1/1993 | Truckai . |
| 5,178,158 | 1/1993 | de Toledo . |
| 5,180,376 | 1/1993 | Fischell . |
| 5,184,627 | 2/1993 | de Toledo . |
| 5,217,482 | 6/1993 | Keith . |
| 5,248,305 | 9/1993 | Zdrahala . |
| 5,313,967 | 5/1994 | Lieber et al. . |
| 5,336,205 | 8/1994 | Zenzen et al. . |
| 5,405,338 | 4/1995 | Kranys . |
| 5,441,489 | 8/1995 | Utsumi et al. . |
| 5,451,209 | 9/1995 | Ainsworth et al. . |
| 5,531,721 | 7/1996 | Pepin et al. . |
| 5,538,513 | 7/1996 | Okajima . |
| 5,545,151 | 8/1996 | O'Connor et al. . |
| 5,569,218 | 10/1996 | Berg . |

REINFORCED CATHETER WITH A FORMABLE DISTAL TIP

FIELD OF THE INVENTION

This invention is a surgical device. In particular, it is a section of a catheter which self-forms a selected shape upon application of a modest amount of heat and retains that shape upon cooling and, indeed, upon any reheating. The catheter section includes in its wall a forming member which typically comprises at least one super-elastic alloy woven braid or coil. The forming member may include other materials and components in addition to the super-elastic element of the forming member. The forming member is typically covered by at least an outer polymeric covering which holds the forming member in a first shape prior to the heating step. Upon softening of the outer layer during that heating step, the forming member self-forms into the desired second shape. The catheter section may be used either in its first shape or its second shape or in any transitional shape between the two. The inner lumen of the forming member may contain a second polymeric tubing member. The inner polymeric tubing member is often lubricious.

The catheter sections made according to this invention may be used alone or in conjunction with other catheter sections. The more proximal sections of a catheter assembly using this concept are often substantially stiffer.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons.

Often the target which one desires to access by catheter is within a soft tissue such as the liver or the brain. These are difficult sites to reach. The catheter must be introduced through a large artery such as those found in the groin or in the neck and then be passed through ever-narrower regions of the arterial system until the catheter reaches the selected site. Often such pathways will wind back upon themselves in a multi-looped path. These catheters are difficult to design and to utilize since they must be fairly stiff at their proximal end so to allow pushing and manipulation of the catheter as it progresses through the body, and yet must be sufficiently flexible at the distal end to allow passage of the catheter tip through the loops and increasingly smaller blood vessels mentioned above and yet at the same time not cause significant trauma to the blood vessel or to the surrounding tissue. Further details on the problems and an early, but yet effective, way of designing a catheter for such a traversal may be found in U.S. Pat. No. 4,739,768, to Engelson.

These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

The human vasculature is quite complex. It is believed that each person's vasculature is unique and indeed could be used as an identifying characteristic of an individual. Be that as it may, there are a few times when, irrespective of the fine design of a guidewire and enhanced trackability of a specific catheter may not in combination allow access to a specific site in the human body. Multiple turns through a neurological area or decreasing radius arterial turns may require that the catheter be slightly modified. It is common practice that suppliers of neurovascular catheters provide mandrels so that the distal end of such catheters be shaped using steam or the like prior to introduction into the human body Because of the inherent flexibility of such neurovascular catheters, the modest shaping imparted to the distal tip of the catheter is usually easily straightened by a more substantial region of the guidewire.

The catheter section at hand, of necessity, includes a tubular forming member containing at least some amount of super-elastic alloy. Consequently, it is quite difficult to form these distal tips in an operating theater. It is therefore desirable that some provision be made for providing a shaping function to such supported catheter sections. In this invention, the metallic forming member is; provided with a shape using a heat treatment step and the polymeric material surrounding the catheter is then used to hold the thusly-shaped forming member in another shape. For instance, a crooked or bent shape may be provided to the forming member during the heat treatment step. The overlying polymeric sheath is then used to straighten the forming member and hold it in a non-equilibrium condition. The polymeric material in the outer layer is then heated using, e.g., steam, and the material in the forming member pulls the shape of the catheter assembly over into a form approximating that given the forming member during the heat treatment step. Ideally, the physician is able to use one or the other of the two shapes for the particular involved situation. It is within the ambit of this invention that only a portion of the affected region of the catheter section be heated so to provide some intermediate shape between the first shape and the second heated shape.

This invention is an adaptable one and may be used in a variety of catheter formats. The invention utilizes the concept of combining one or more polymeric tubes with a metallic tubular forming member comprising a super-elastic alloy. The construction technique has the benefit of producing catheter sections having small overall diameters but with exceptional strength, resistance to kinking, and recovery from kinking (even in vivo) should such kinking occur. It may be used with the distal tip either in the first shape or in the post-heated second shape or in any transitional shape between. This catheter may be used in conjunction with a guidewire, but the catheter body may also be used as a flow-directed catheter with the attachment of a balloon or in combination with a specifically flexible tip, as is seen, for instance, in U.S. Pat. No. 5,336,205 to Zenzen et al., the entirety of which is incorporated by reference.

The use of a stiffening section in a catheter body is not a novel concept. Typical background patents are discussed below. However, none of these documents have used our concept to produce a catheter section with the forming capabilities of this invention.

Multi-Wrap Catheters

There are a number of catheters discussed in the literature which utilize catheter bodies having multiply-wrapped reinforcing material. These catheters include structures having braided bands or ones in which the spirally wound material is simply wound in one direction and the following layer or layers are wound in the other.

Krippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer.

Similarly, U.S. Pat. No. 3,416,531, to Edwards, shows a catheter having braiding-edge walls. The device further has additional layers of other polymers such as TEFLON and the like. The strands found in the braiding in the walls appear to be threads having circular cross-sections. There is no suggestion of constructing a device using ribbon materials. Furthermore, the device is shown to be fairly stiff in that it is designed so that it may be bent using a fairly large handle at its proximal end.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands which are braided, that is to say, bands which are spiraled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multi-layered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is a polyaramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire. It would not meet the flexibility criteria required of the inventive catheter described herein.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it loo be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are would throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches.

Another variation which utilizes a catheter wall having helically placed liquid crystal fibrils is found in U.S. Pat. No. 5,248,305, to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

Single-Layer, Reinforced Catheters

There are a variety of catheters which, unlike the devices discussed above, utilize but a single layer of reinforcing material.

For instance, U.S. Pat. No. 243,396 to Pfarre, patented in June of 1881, shows the use of a surgical tube having a wire helix situated within the tube wall. The wire helix is said to be vulcanized into the cover of the device.

U.S. Pat. No. 2,211,975, to Hendrickson, shows a similar device also comprising a stainless steel wire 15 embedded in the inner wall of a rubber catheter.

U.S. Pat. No. 3,757,768, to de Toledo, shows a "unitary, combined spring guide-catheter that includes an inner wall portion formed as a continuous helical spring with the helices in contact with each other and an outer wall portion formed from an inert plastic material enclosing the spring in such a manner as to become firmly bonded to the spring while having its outer surface smooth". There is no suggestion to separate the windings of the coil in any fashion.

U.S. Pat. No. 4,430,083 describes a catheter used for percutaneous administration of a thrombolytic agent directly to a clot in a coronary artery. The device itself is an elongated, flexible tube supported by helically wound wire having a specific cross-sectional shape. The wire is wound into a series of tight, contiguous coils to allow heat shrinking of tubing onto the outside of the wire of the shape of the outer surface of the wire as wound into the helix provides tile heat-shrunk tubing with footing for a tight fit.

U.S. Pat. No. 4,657,024, to Coneys, shows a catheter which employs a set of helical strips within the wall of the catheter. However, the helical strips are of a radio-opaque material, e.g., fluorinated ethylene-propylene. It is not clear that the blended radio-opaque material necessarily provides any physical benefit other than the ability to allow the catheter shaft to be seen when viewed with a fluoroscope.

U.S. Pat. No. 4,737,153, to Shimamura et al., describes a device which is characterized as a "reinforced therapeutic tube" and which uses a spiral reinforcing material embedded within the wall of the device.

U.S. Pat. No. 5,069,674, to Fearnot et al. (and its parent, U.S. Pat. No. 4,985,022), shows a small diameter epidural catheter having a distal tip made up of a stainless steel wire which is helically wound and placed within a tubular sheath or tube.

Similarly, U.S. Pat. No. 5,178,158, to de Toledo, shows what is characterized as a "convertible wire for use as a guidewire or catheter". The patent describes a structure which comprises an interior wire or spring section shown, in the drawings, to be of generally rectangular cross-section. Outer layers of the device include a polyamide sheath placed adjacent to the helical coil at the proximal end of the catheter (see column 4, lines 64 and following). The device also comprises an outer sheath 40 of Teflon that extends from the proximal end 12 to the distal end 14 of the device. The overlying sheath 40 may extend or overhang at the proximal or the distal end of the catheter. The distal tip portion 13 is said to be "flexible, soft, and floppy". The PCT Published Application corresponding to this patent is WO 92/07507.

U.S. Pat. No. 5,184,627 shows a guidewire suitable for infusion of medicaments to various sites along the guidewire. The guidewire is made up of a helically wound coil having a polyamide sheath enclosing its proximal portion and a Teflon sheath tightly covering the entire wire coil. The coil is closed at its distal end.

U.S. Pat. No. 5,313,967, to Lieber et al., shows a medical device, a portion of which is a helical coil which apparently may include an outer plastic sheath in some variations. Apparently, a secondary helix of a somewhat similar design (in that it is formed by rotating a flat wire or the like along its longitudinal axis to form a screw-like configuration) is included within the helical coil to provide axial pushability and torque transmission.

U.S. Pat. No. 5,405,338, to Kranys, describes a helically wound catheter incorporating a shaft component having a helically wound coil with a skin or webbing supported by the coil. The skin or webbing is said to contribute "negligibly to the resistance of the catheter to axially directed compressive forces. . ." The catheter may include an inner, taut skin component.

The PCT application, WO 93/15785, to Sutton et al., describes kink-resistant tubing made up of a thin layer of an encapsulating material and a reinforcing coil. As is shown in the drawings, the supporting material is embedded within the wall of the tubing in each instance.

The PCT application bearing the number WO 93/05842, to Shin et al., shows a ribbon-wrapped catheter. The device is shown as a section of a dilatation catheter. The inner section 34 is a helically wound coil and is preferably a flat wire. See, page 6, lines 25 and following. The coil is then wrapped with a heat-shrunk jacket 34 formed of low-density polyethylene. A lubricious material such as a silicone coating may then be placed on the inner surface of the spring coil to "enhance handling of the guidewire". It is also said, on page 6 of the document, that the "entire spring coil, before it is wound or jacketed, may be coated with other materials such as Teflon to enhance lubricity or provide other advantages. In some embodiments, the spring coil has been plated with gold."

Endoscope Structures

Various endoscopic structures, used primarily in sizes which are larger than endovascular catheters utilize structures including stiffener materials.

U.S. Pat. No. 4,676,229, to Krasnicki et al., describes an endoscopic structure 30 having an ultra-thin walled tubular substrate 31 formed of a lubricious material such as TEFLON. The structure contains a filament supported substrate. The filament is coated with and embedded into a filler material, typically an elastomeric material. A highly lubricious outer coating 35, all as shown in FIG. 2, forms the outer layer of the device. FIG. 3 in Krasnicki et al., describes another variation of the endoscopic device in which a different selection of polymer tubing is utilized but the placement of the filamentary support remains varied in an intermediate material of an elastomer. In some variations of the device, the filament is strongly bonded to the inner tubular substrate using an adhesive 37 "such as an epoxy cement having sufficient bond strength to hold the :filament to the substrate as it is deformed into a tight radius." See, column 3, lines 50 and following.

U.S. Pat. No. 4,899,787, to Ouchi et al. (and its foreign relative, German Offenlegungschrift DE-3242449) describes a flexible tube for use in an endoscope having a flexible, basic tubular core structure made up of three parts. The three parts are an outer meshwork tube, an intermediate thermoplastic resin tube bonded to the outer meshwork tube, and an inner ribbon made of a stainless steel or the like which is adherent to the two polymeric and meshwork tubes such that the resin tube maintains an adherent compressive pressure in the finished flexible tube. The patent also suggests the production of an endoscope tube having "flexibility which varies in step-wise manner from one end of the tube to the other . . . [and is produced] by integrally bonding two or more thermoplastic resin tube sections formed of respective resin materials having different hardnesses to the outer surface of the tubular core structure . . .". See, column 2, lines 48 and following.

U.S. Pat. No. 5,180,376 describes an introducer sheath utilizing a thin, flat wire metal coil surrounded only on its exterior surface with a plastic tube of coating. The flat wire coil is placed there to lower the "resistance of the sheath to buckling while minimizing the wall thickness of the sheath." A variation using two counterwound metal ribbons is also described.

European Patent Application 0,098,100 describes a flexible tube for an endoscope which uses a helically wound metallic strip having a braided covering contiguous to the outer surface of the coil and having still further out a polymeric coating 9. Interior to the coil is a pair of slender flexible sheaths which are secured to a "front-end piece 10" by soldering.

Japanese Kokai 2-283,346, describes a flexible endoscope tube. The tubular outer shell is made up of two layers of a high molecular weight laminated material. The tube also has an inner layer of an elastic material and interior to it all is a metallic ribbon providing stiffening.

Japanese Kokai 03-023830, also shows the skin for flexible tube used in an endoscope which is made up of a braid 3 prepared by knitting a fine wire of a metal with a flexible portion 2 which is prepared by spirally winding an elastic belt sheet-like material and a skin 4 with which the whole outer surface of the device is covered. The document appears to emphasize the use of a particular polyester elastomer.

Japanese Kokai 5-56,910, appears to show a multi-layered endoscope tube made up of layers of the spiral wound metallic ribbon covered by a polymeric sheath.

French Patent Document 2,613,231, describes a mrledical probe used with an endoscope or for some other device used to stimulate the heart. The device appears to be a helix having a spacing between 0 and 0.25mm (See page 4, line 20) preferably rectangular in cross section (See Page 4, Line 1) and of a multi-phase alloy such as M35N, SYNTACOBEN, or ELGELOY (See Page 4).

German Offenlegungschrift DE-3642107 describes an endoscope tube, formed of a spiral tube, a braid formed of fibers interwoven into a net (which braid is fitted on the outer peripheral surface of the spiral tube), and a sheath covering the outer peripheral surface of the braid.

None of the noted devices appear to have a distal tip which changes from a first desired shape to a second desired shape upon application of heat and remain in that second shape.

SUMMARY OF THE INVENTION

The invention here is a catheter section. It is a portion of a catheter made up of a tubular forming member having a first form and a second form. The second form is different from the first form. Placed about the tubular forming member is a heat softenable polymeric covering. The covering is able to maintain the forming member in what could be characterized as a non-equilibrium or a stress first form. The catheter section comprising at least these two components is adapted so that should the polymeric covering be sufficiently softened, the forming member will, because of its contained internal stress, form into the second form mentioned above.

The tubular forming member may be metallic or polymeric. Preferably, though, the forming member comprises a super-elastic alloy. The forming member may be a coil or coils or a woven or unwoven braid. Super-elastic alloy ribbon braids are preferred because of their ability to retain non-elastic strain and return to a prior form upon release of the polymeric restraint.

The preferred super-elastic alloy preferably comprises nickel and titanium, perhaps with a small amount of an iron group metal. The super-elastic alloy most preferably has a transition temperature below 0° centigrade. Higher transition temperatures may be tolerated and the use of a temperature memory of the alloy may be utilized if so desired. However use of the temperature memory characteristics of the super-elastic alloy is not a central feature of the invention.

The catheter section is desirably used as a distal portion of catheter assembly. Obviously, it need not be.

DESCRIPTION OF THE INVENTION

This invention includes a catheter section made up of at least a tubular forming member and a flexible, typically polymeric, outer member. Although the outer member and the forming member may be in contiguous contact, such need not be the case. The forming member may be made of a braid or coil or a combination of one or more of each of these components. As noted elsewhere, the forming member placed in this catheter section is treated in such a way that if has a second shape in its equilibrium condition. The forming member is held in a first shape—a non-equilibrium shape—different from the second shape, by the presence of the outer layer. The catheter section is, however, self-forming from one shape to the other through the application of heat to the outer restraining member due to the softening of that layer or, depending upon the polymer chosen, passage of the polymeric material through $T_g^°$. The catheter section may be the distal portion of a catheter assembly or, indeed, may be placed in any location within the catheter assembly.

Figure 1A:
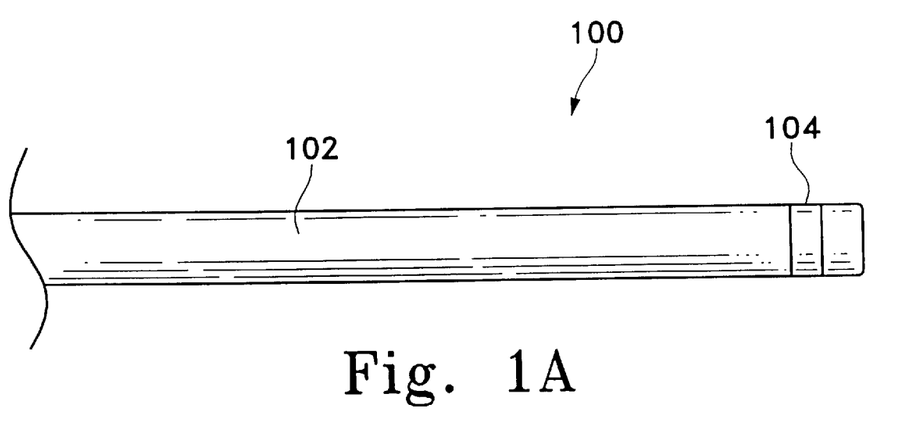
FIG. 1A shows a partial side view of a distal catheter tip in a first configuration or first form.

As an illustration only, FIG. 1A shows a catheter section made according to this invention. In this variation, the catheter section (100) may be seen as an exterior surface and a marker ribbon (104). The outer polymeric covering required by this invention may be the outer tubular member (102) shown in FIGS. 1A and 1B or it may be interior to the surface (102).

Figure 1B:
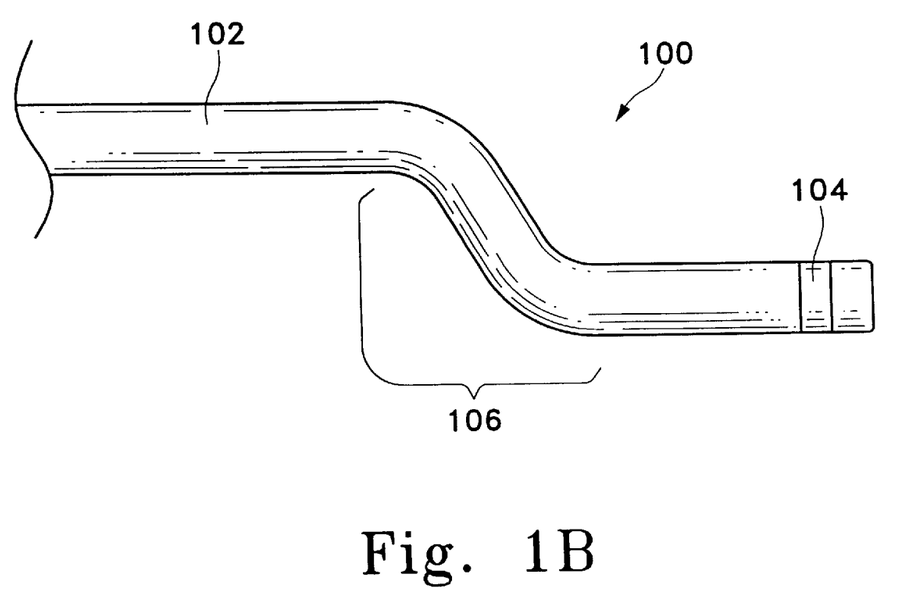
FIG. 1B shows the distal catheter tip of FIG. 1A in a second configuration or second shape.

FIG. 1B shows that the same distal catheter section (100) shown in FIG. 1A but after heating to allow the unshown forming, member to self-form into the second form (106).

It should be understood that the shapes noted in FIGS. 1A and 1B are only suggestive of the types of shapes that may be used according to this invention. Any first or second shape may be used in accordance with this invention. It may be desirable, for instance, that the first (or non post-heating) shape be a simple 45° or 90° or shepherd's crook shape and a second shape after heating be straight or vice versa.

Figure 2:
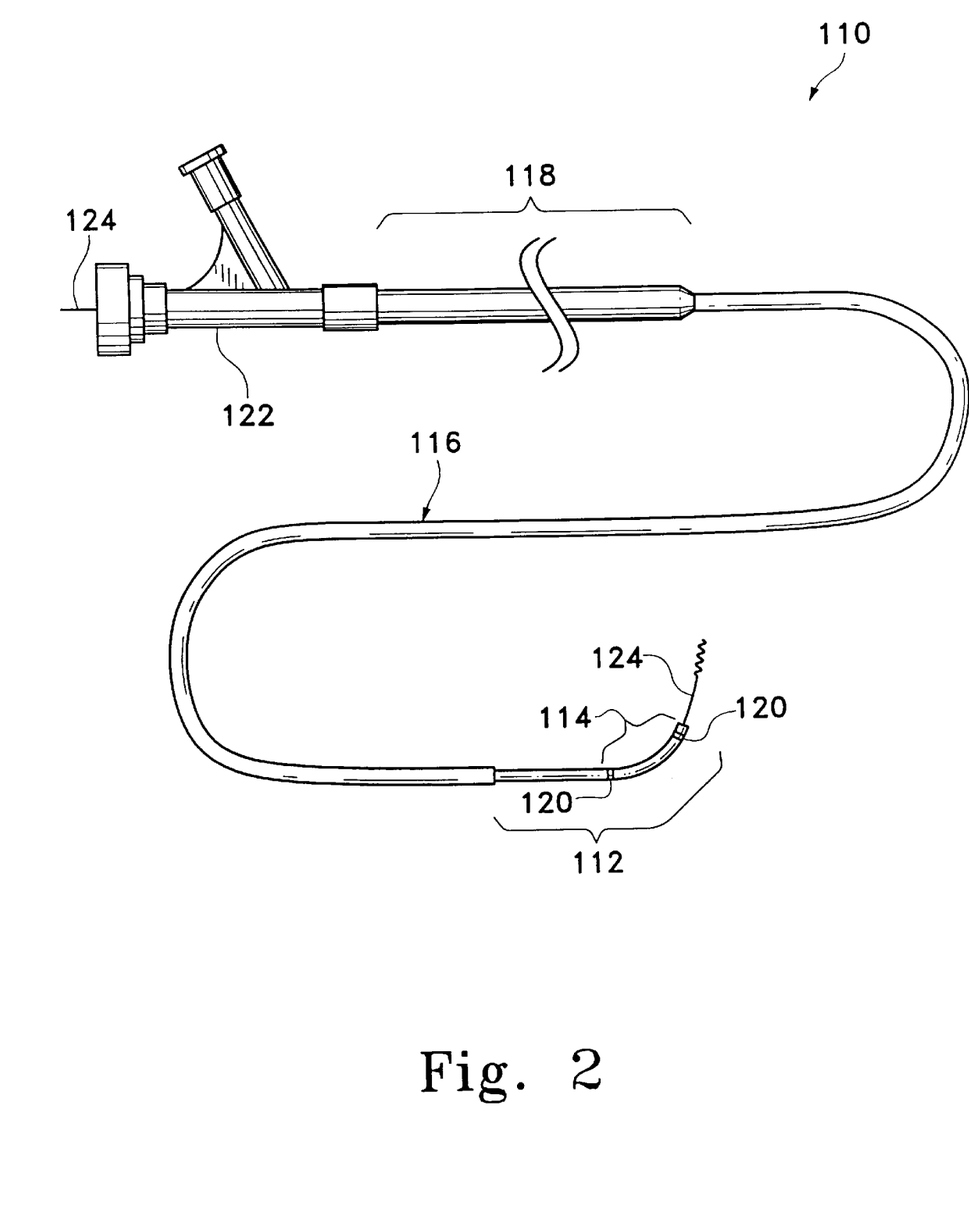
FIG. 2 shows a plan view of a catheter assembly which may include a catheter section made according to the invention.

A typical multi-section catheter (110) incorporating the concepts of this invention is shown in FIG. 2. Such a catheter is described in more detail in U.S. Pat. No. 4,739,768 to Engelson (the entirety of which is incorporated by reference) as particularly suitable for neurological and peripheral vascular applications. Such a catheter is also suitable for less demanding regions of the body such as the heart. Difficulty which has arisen as higher demands for length have been placed on these catheters is that the catheter itself is sometimes unable to traverse a turn in far distal regions of the catheter. This is so because the diameter of the distal section of the catheter necessarily has become smaller as more distal regions are reached. Although the ability to transmit torque from the proximal end of the catheter to the distal is very much improved due to the use of braiding such as is described in conjunction with this invention, sometimes that braiding is not sufficient. Providing a small amount of shape to the distal section of the catheter can mean the difference between a successful procedure and one that is not as successful.

The typical configuration shown in FIG. 2 has a distal section (112) having significant flexibility and, in this instance, having a portion (114) which has assumed a secondary shape. The catheter (110) shown in FIG. 2 also has an intermediate section (116) which is typically less flexible than distal section (112) and also has a long proximal section (118) which in turn is least flexibly. The distal section (112) is quite flexible and soft to allow deep penetration into the soft tissues of the body, e.g., the brain and the liver. Various known and often necessary accessories to the catheter assembly (100) one or more radiopaque bands (120) at the distal region to allow viewing of the position of the distal most portion of the catheter assembly (110) or the portion of the catheter (114) having a specific shape under fluoroscopy and a luer assembly (122) for guidewire (124) and fluids access are also shown in FIG. 2.

Typical dimensions of a catheter assembly (110) made according to this invention are:

Overall Length: 60 cm–250 cm
Proximal Section (118): 60 cm–185 cm
Intermediate Section (116): 20 cm–50 cm
Distal Section (112): 2.5 cm–30 cm These dimensions are not critical to this invention and are selected both as a function of the malady to be treated and selection by the designer formulating a specific design for such a malady. Typical of the catheters made using this invention are those in the two French to five French range. The inner diameter of such catheters is generally in a range of five mils (0.005") to forty-five mils (0.045").

A catheter assembly (110) made using this inventive concept need not be of three sections of increasing stiffness as is shown in FIG. 2, however, the catheter may be of two discrete sections or may be of four or more discrete sections of differing flexibility. Through judicious choice of physical parameters for the catheter sections, the components may also have varying physical parameters (e.g., lubricity, flexibility, wall thickness, inner or outer layer member or compositions, etc.) within each section.

Typically, although not necessarily, when a three section catheter assembly (110) as shown in FIG. 2 is desired, the most proximal section (118) is the "more proximal" or "stiff" section described herein. Again, although not necessarily, when a three section catheter assembly is desired, the most distal section (112) is the "more distal" or "least stiff" section. The midsection (116) mail be either more distal or more proximal depending upon the situation of description herein. However, it should be understood that it is a rare infusion catheter having a more distal section which is stiffer than any of its more proximal sections.

Figure 3:
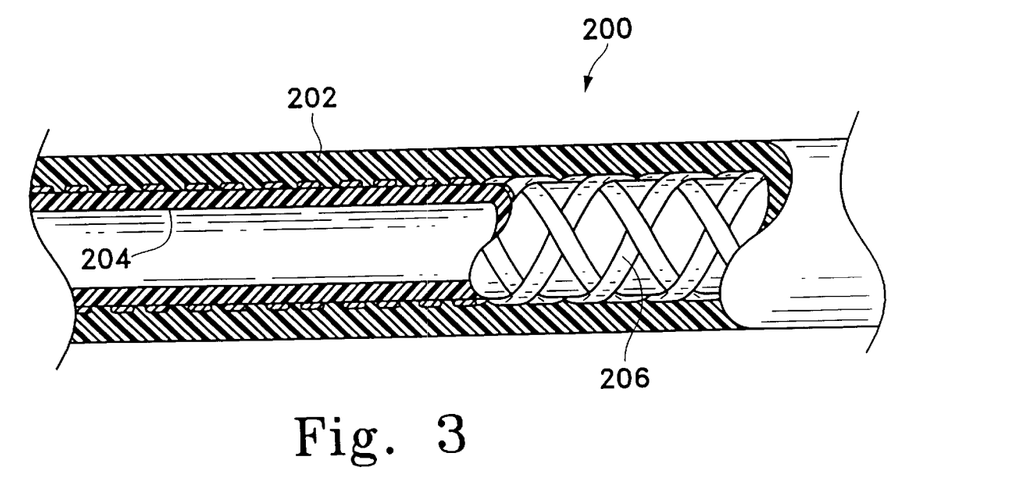
FIG. 3 shows a partial cross section of an inventive catheter section made according to the invention.

FIG. 3 shows a magnified partial cross section of a catheter body or section (200) showing the most basic aspects of one variation of this invention. As shown in FIG. 3, the catheter body section (200) has an outer covering member (202) and an inner liner member (204). Situated between outer member and inner member (204) is the stiffening member (206). In this instance, stiffening member (206) is a woven braid of ribbon shaped materials. Although this a highly preferred variation, the inner liner member (204) is optional. That variation will be discussed with regard to other figures below. As shown in FIG. 3, both outer member (202) and inner member (204) are polymeric. Although they may be made of materials which tack to each other upon heating, they need not be. In some instances, they may contain components which act in a manner of adhesives, or are adhesives, but, again such is not necessary. Typically, for the simple variation shown in FIG. 3, the outer covering member (202) is of a material which is heat shrinkable (e.g., low density polyethylene preferably as a copolymer containing 5–200% ethylvinylacetate) or may be otherwise coated on to the structure (e.g., polyurethanes), on to inner member (204) and woven braid (206). Preferred polymeric materials for inner liner (204) included polyethylene, polypropylene, polyvinylchloride (PVC), ethylvinylacetate (EVA), polyurethanes, polyamides, polyethyleneterephthalate (PET), and their mixtures and copolymers. Preferred materials both for the inner member (204) and the outer covering member (202) include polytetrafluoroethylene (PTFE or TFE), ethylene-chlorofluoroethylene (ECTFE), fluorinated ethylenepropylene (FEP), polychlorotrifluoroethylene (PCTFE), polyvinylfluoride (PVF) or polyvinylidenefluoride (PVDF). Especially preferred for the inner member (204) is PTFE or TFE.

We have found that when a fluoropolymer is used as an inner tubing member (204), it is useful to etch the outside surface of the member to provide a good mechanical and chemical surface to which adjacent polymers will adhere. Certain procedures, using, for instance, aliphatic hydrocarbons and sodium metal as the etching solution are known to be effective.

Another useful class of polymers are thermoplastic elastomers, including containing polyesters as components. Typical of this class is HYTREL. Additionally, an adhesive may be coated on to the outer su-face of the inner tubing (204) or on the inner surface of outer tubing (202). Polyesters and polyimides are especially suitable as these adhesives.

An outer covering of polyethylene or of EVA or their mixtures, copolymers, etc. is an excellent choice for the outer covering member (202). The polymer used as the outer covering (202) is typically pre-extruded into tubing of an appropriate size and thickness and then cross-linked using ionizing radiation to raise the melt temperature of the resulting tubing. The tubing is then inflated and perhaps stretched to give the included polymer a specific molecular orientation. The tubing, so treated, may then be slipped over a combination of inner liner (204) and woven braid (206) and heat shrunk into place.

As noted above, a variety of other polymers may be used, depending on the use to which the catheter section is placed. For instance, if the catheter section (200) is used as a proximal section, the outer tubing may be a polyimide, a polyamide (such as the "Nylons"), high density polyethylene (HDPE), polypropylene, PVC, various fluorocarbon polymers, polysulfones, or the like. Blend, alloys, mixtures, copolymers and block copolymers of these materials and others are suitable if so desired.

If a more flexible section (200) is desired, the outer tubing member (202) may also be a more flexible material such as a polyurethane, LDPE, PVC, THV, etc. And other polymers of suitable softness or modulus of elasticity.

FIG. 3 shows the results of either heat shrinking the outer tubing member (202) on to the assembly of inner liner tubing (204) and woven braid (206) are dipping the subassembly of the inner liner (204) and braid (206) in to a molten or latex liquid of the outer region. Contact regions between the outer covering member (202) and inner liner member (204) are shown in interstices, between the open weave of the woven braid (206). Such contact is, however, not always necessary. Although the open area between turns of the braid are not absolutely necessary as a means of allowing contact between the inner liner (204) and the outer covering (202), such is quite desirable when only two layers are used. Furthermore, when the outer covering member (202) is introduced on to the outer surface of the catheter section (202) by dipping using a molten liquid or latex liquid bath, the contact is largely inevitable.

We have found that when using the highly desirable polyurethane as either the outer covering member (202) per se or as an inner portion of the outer covering member (202), e.g., beneath a further exterior polyethylene layer, a suitable method for applying the polyurethane entails placement of pre-formed polyurethane tubing over the forming element or woven braid (206), placement of a polyethylene "shrink-wrappable" tubing over the polyurethane tubing, and healing the combination to pull the polyurethane down to the braid surface using the shrink wrap action of the polyethylene tubing as the mover. The polyethylene layer may be removed or left in place The wall thickness of the outer tubing member (202) may be as thin as 0.5 mils and as thick as 10 mils, depending upon catheter usage, section of the catheter chosen, polymer choice and the style of catheter.

Typically, a wall thickness of the inner liner will be between 0.5 and 3.0 mils. These dimensions are obviously only provided for guidance and each specific catheter variation must be carefully designed for the specific purpose to which it is placed.

Each of the polymers noted herein may be used in conjuctions with radiopaque filler materials such as barium sulfate, bismuth trioxide, bismuth carbonate, powdered tungsten, powdered tantalum, and the like, so that location of various portions of the catheter sections may be radiographically visualized within the human body.

It is within the scope of this invention to have multiple polymeric layers (202) exterior of the forming member (206) or its analogs below as well as multiple polymeric liner members interior thereto. Furthermore, it is within the scope of the invention to include multiple forming member components, e.g., woven braids, nonwoven braids, coils of ribbon, wire, or other fiber between or amongst the various polymeric layers.

It is also within the scope of this invention to coat it least one of the exterior surface of outer member (202) and the inner surface of inner liner (204) with a lubricious layer, which layer is either chemically bonded lo or is physically coated on the relevant surface.

The woven braid (206) found as the forming member in the FIG. 3 variation may be made of a variety of materials. The single overlying requirement is that the material be able to take a "set" and retain sufficient residual stress once so formed and restrained in an outer covering which, upon softening of that outer covering, will relax and form the "set" shape. A variety of engineering plastics or liquid crystal polymers (LCP), aromatic copolyesters with a tightly ordered structure that is self-reinforcing. Some stainless steels are also suitable, although careful balancing of strength and ability to form a shape without elastic reformation of the shape because of coating with the outer layer must be made. Most preferred of all materials is a class of alloys known as super-elastic alloys. These alleys are able to survive a significant amount of stress without elastic deformation. Although a number of these materials are known to the industry, nickel-titanium alloys are preferred because of their ready availability and their prior significant use in medical devices. Nickel-titanium alloys having super-elastic properties and known generically as nitinol were discovered by the U.S. Naval Ordnance Laboratory several decades ago. The early work in these materials is shown in U.S. Pat. No. 3,174,851 to Buehler et al., U.S. Pat. No. 3,351,463 to Rozner et al., and 3,753,700 to Harrison et al. Commercial alloys containing up to about 8% or more, preferably up to about 3% or more, of one or more members of the iron group of metals, e.g., Fe, Cr, Co, etc., are considered to be encompassed within this class of super-elastic nickel-titanium alloys suitable for this inventive surface. Most preferred are super-elastic nickel-litanium alloys containing 1.5 to 2.5% Cr and having a transition temperature of less than 25° C. and most preferably less than about 0° C. Most preferred are materials which do not undergo a temperature-induced phase transition in the temperature range of use.

Mixtures of these materials may be used in the braids and coils making up the forming members of this invention The braid shown in FIG. 3 is a woven braid. The braids used via this invention may be made using commercially available braiders. The term "braid" is meant in this instance to include tubular constructions in which the ribbons making up the construction are woven in a radial in-and-out fashion so that they cross to form a tubular member defining a single lumen. The braids may be made up of a suitable number of ribbons, typically 6 or more. Ease of production on a commercial braider typically results in braids having 8 or 16 ribbons.

Metallic ribbons that are suitable for use in this variation of the invention are desirably between 0.25 mils and 3.5 mils in thickness and 2.5 mils and 12 mils in width. By the term "ribbon," we intend to include elongated shapes, the cross-section of which are not square or round and may typically be rectangular, oval or semi-oval.

They should have an aspect ratio of at least 0.5 (thickness/width). In any event for super-elastic alloys, particularly nitinol, the thickness and width may be in the lower end of the noted ranges. Currently desirable ribbons included sizes of 0.75 mil by 4 mils, 1 mil by 3 mils, 1 mil by 4 mils, 2 mils by 6 mils and 2 mils by 8 mils.

The ribbons making up the braid (206) shown in FIG. 3 may also contain an amount of non-super-elastic alloy materials. Although metallic ribbons are preferred as the ancillary materials because of their strength-to-weight ratios, fibrous materials (both synthetic and natural) may also be used. Preferred, because of cost, strength and ready availability, are stainless steels (SS304, SS306, SS308, SS316, SS318, etc.) and various tungsten alloys. In certain applications, particularly in use in smaller diameter catheter sections, malleable metals and alloys, e.g., gold, platinum, palladium, rhodium, etc., may be employed. A platinum alloy with a few percent of tungsten is preferred partially because of its radio-opacity. Suitable non-metallic ribbons include high performance materials such as those made of polyaramids (e.g., Kevlar) and carbon fiber.

The braid shown in FIG. 3 has a nominal pitch angle of 45°. Clearly, the invention is not so limited. Other braid angles from 20° to 60° are also suitable. An important variation of this invention is the ability to vary the pitch of the braid either at the time the braid is woven or at the time the braid is included in the catheter section or sections.

After the braid is woven, the section which is to be given a second form may be cleared of the straight mandrel used to weave the tubing and a shaped mandrel inserted. The shaped mandrel has a shape of the second form of the catheter section as discussed above. The mandrel and woven braid are then heat treated at an appropriate temperature and time to impart the desired shape to the tubular braid. The temperature and time needed are obviously a function of the material chosen but, for instance, a Cr-containing nickel-titanium super-elasltic alloy which has been rolled into a 1 by 4 mil ribbon and formed into a 6-member braid may be heated to a temperature of 550–750° F. for a few minutes to impart the desired shape to the forming member.

It may be observed that woven super-elastic alloy braids and coils which have not been so heat treated will themselves unravel given the opportunity. Consequently, it may be desirable to heat treat such super-elastic alloy braids or coils in a sequence of steps. For instance, the forming member and the straight mandrel may be heat treated in a first step and only then would the section of the mandrel underlying the tubular forming member be formed either by removal and replacement with a shaped mandrel or the section of mandrel be bent into the desired shape for subsequent heat treatment.

Once the forming member has been so formed into the second configuration or form, it must then be re-formed into the first form. Although not absolutely necessary for this invention, the first form may be straight; other forms may be desirable. Indeed, as noted above, the first form may be non-straight and the second form generally linear, if so desired.

In any event, the forming member is placed on a mandrel having the shape of the first form. A polymeric layer of a suitable type, thickness, stiffness, etc. is then placed on the exterior of the forming member. The polymers discussed above are appropriate for such layer. The polymeric layers should be softenable at temperatures in the neighborhood of 175–225° F. to allow the catheter section to assume the second form using steam-forming streams often available in surgical theatres. Such a high softening temperature also allows for maintenance of the shape during packaging, sterilization, shipping operations, and during storage at user sites.

Finally, the inner layer (204) may, instead of being a polymeric layer, be a coil of wire or ribbon so to provide a hard surface in which a guidewire may easily pass. This is not a desired variation because of the difficulty in providing sufficient outer polymeric tubing to preserve the first shape.

Figure 4:
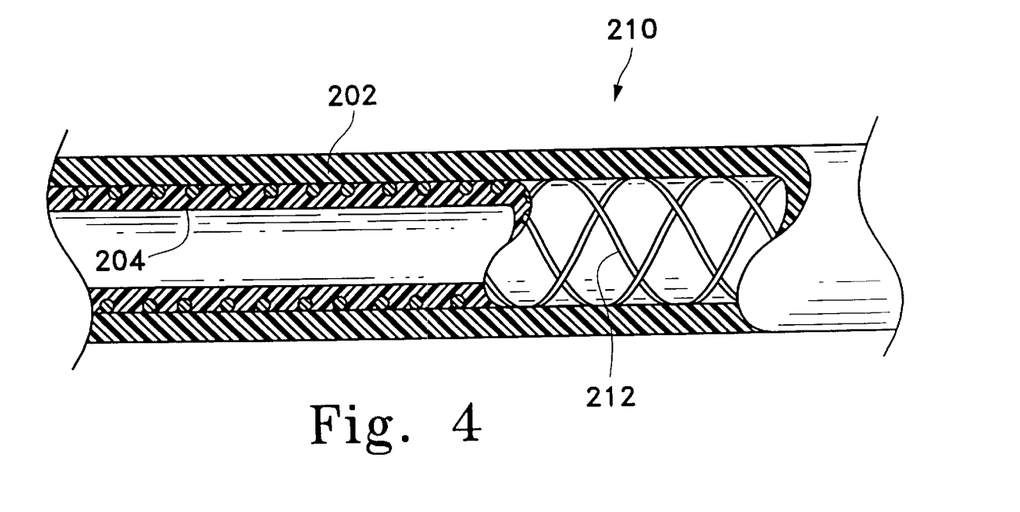
FIG. 4 shows a partial cross section of an inventive catheter section made according to the invention.

FIG. 4 shows another variation (210) of the inventive catheter section in which the outer covering (202) and the inner liner (204) are depicted to be the same. The braid (212), however, is a woven braid of a cylindrical material such as wire or thread. The materials making up the woven braid (212) may be the same as those used in discussing the FIG. 3 variation above.

This variation has good points and bad points. Because of the use of the material having a somewhat more round cross-section than the ribbon found in the FIG. 3 variation, the overall profile of the catheter device can be a bit larger.

Figure 5:
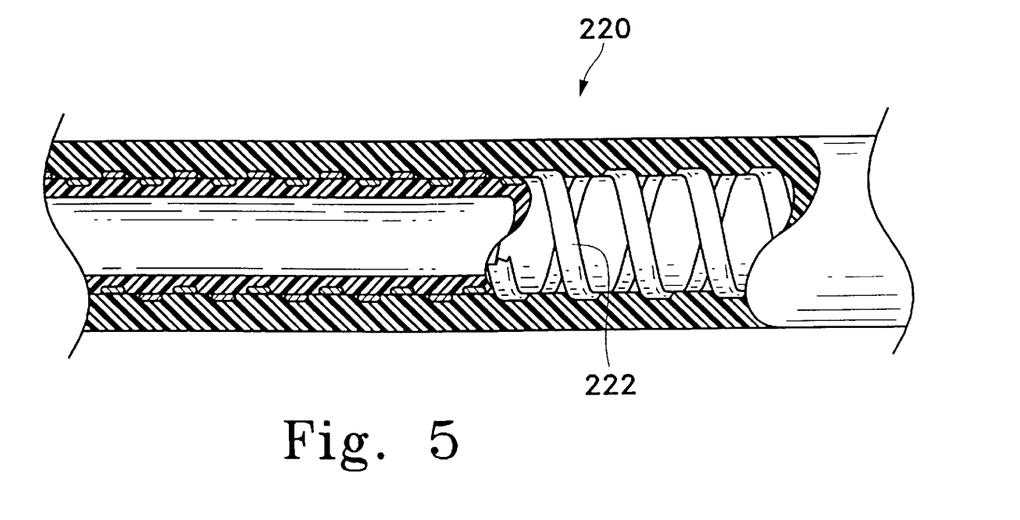
FIG. 5 shows a partial cross section of an inventive catheter section made according to the invention.
Figure 6:
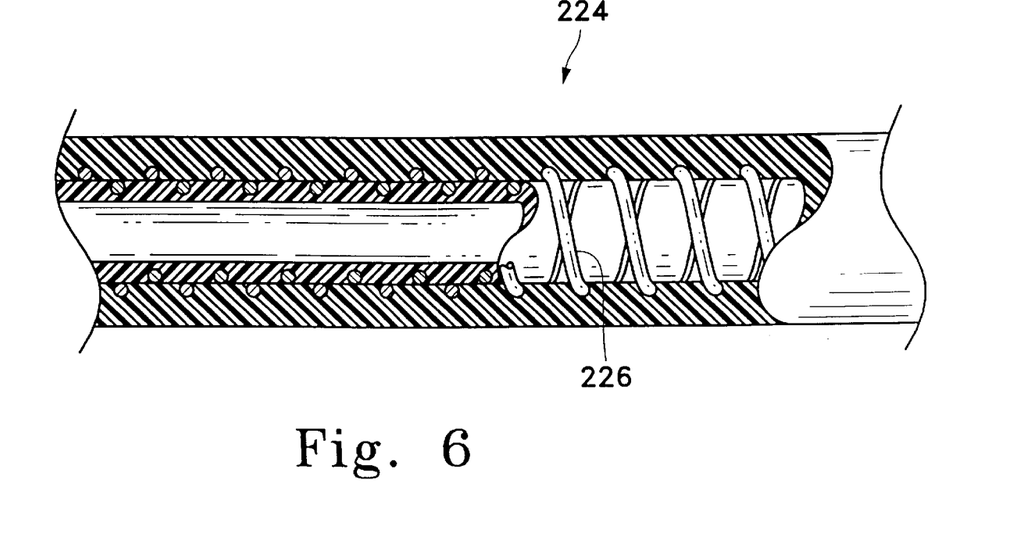
FIG. 6 shows a partial cross section of an inventive catheter section made according to the invention.

FIG. 5 depicts a further variation of catheter section (220) similar in construction to those found in FIGS. 3 and 4. In this variation, the braid (222) is not "woven," but instead is a number of coils which are not w oven in an in-and-out fashion as were the braids of the variations of FIGS. 3 and 4. One or more inner coils are wound onto an inner mandrel or tubing of some kind and desirably a similar number of outer ribbon coils are wound exterior to the other handed inner coils. These devices are somewhat harder to construct in that the coils have no inherent way of maintaining their structural cohesiveness in the way that a woven braid has. Nevertheless, the structure of this ribbon coil-based catheter section and the similar variation (224) shown in FIG. 6 using a wire or strand-based unwoven coils (226) are acceptable alternatives to the preferred variation shown in FIG. Nos. 3 and 4.

Figure 7:
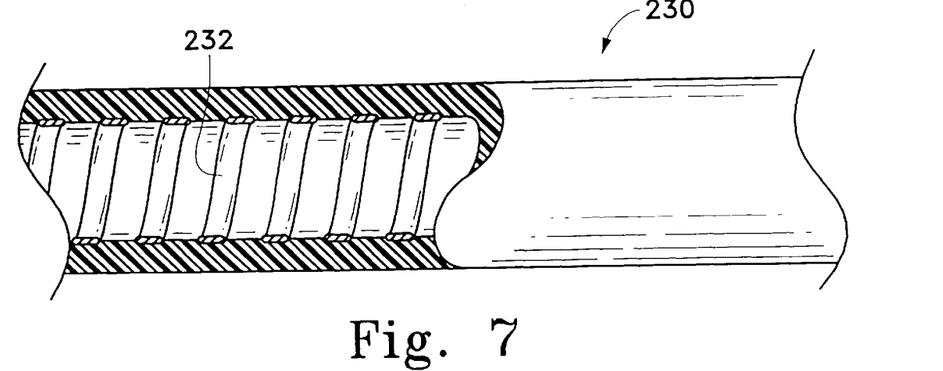
FIG. 7 shows a partial cross section of an inventive catheter section made according to the invention.

FIG. 7 shows still another variation (230) of the inventive catheter section. In this variation, two independent concepts are shown. The first concept is the use of a single interior coil (232) as the stiffening member. The coil is comprised of one or more ribbons comprised of the materials spoken of above. Further, the catheter section (230) has no inner polymeric tubing member. Instead, the stiffening member (232) provides an open lumen from one end to the other. The use of a single coil and the use of a coil and the use of a stiffening member having no inner liner are the two independently useable concepts to be appreciated from this variation.

Figure 8:
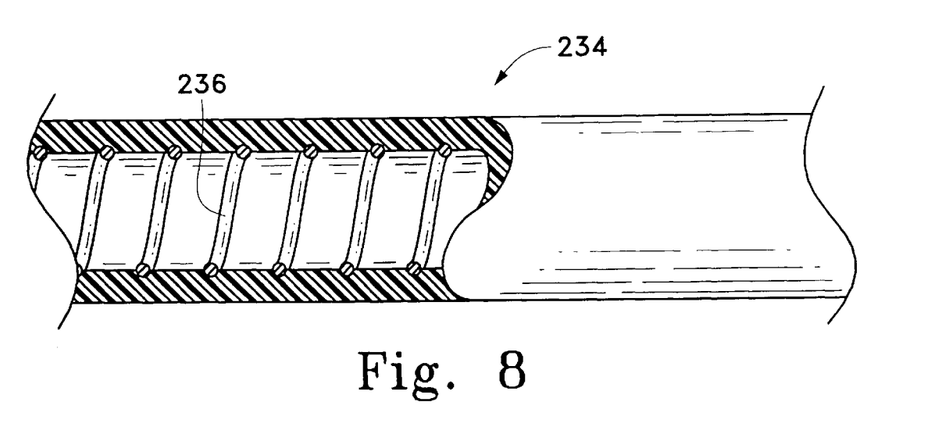
FIG. 8 shows a partial cross section of an inventive catheter section made according to the invention.

FIG. 8 shows a variation (234) which, instead of the one or more ribbon coils (232) used in FIG. 7, uses one or more coils having round cross-sectional component areas.

Figure 9:
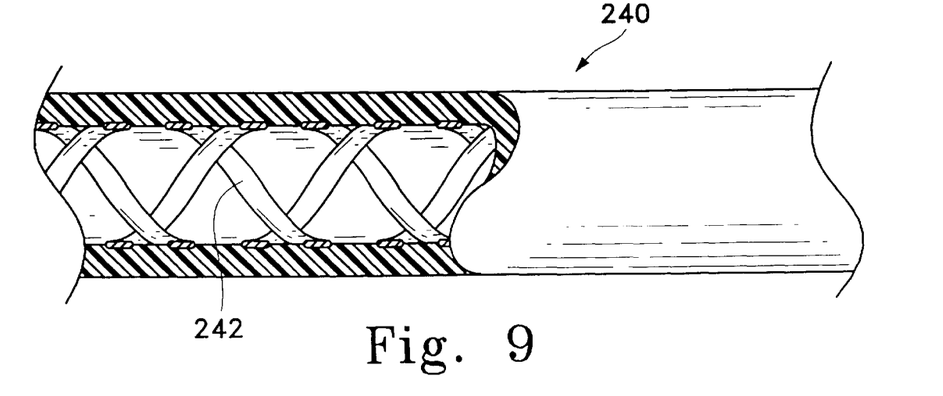
FIG. 9 shows a partial cross section of an inventive catheter section made according to the invention.

Finally, FIG. 9 shows a variation of the inventive device in which a woven braid (242) is used in the manner of the coils ((232) in FIG. 7, (236) in FIG. 8) and forms an open lumen in the catheter section (230).

We wish to emphasize that although these catheter sections have special use in the distal section of catheters which are used in neurological and other soft organ applications, the catheter section may be used at any point where a change in shape would be desirable through the application of a modest amount of heat. Indeed, it may be desirable to have a number of these sections of changeable configurations placed through the length of a catheter in certain situations. For instance, when using this neurological catheter in cardiovascular service, it may be desirable to have a pair or more of sites in the catheter so that the device forms a large shepherd's hook so to allow easy access of distal regions of cardiac arteries.

This invention has been described and specific examples of the invention have been portrayed. The use of those specifics is not intended to limit the invention in any way. Additionally, to the extent that there are variations of the invention which are within the spirit of the disclosure and yet are equivalent to the invention as found in the claims, it is our intent that those claims cover the variations as well.

We claim as our invention:

1. A catheter section comprising:
    a.) a tubular forming member having a first form and a second form different from the first form, and
    b.) a heat softenable polymeric covering exterior to said tubular forming member, said covering maintaining said tubular forming member in said first form until subjected to a heating step,
    wherein upon heating said catheter section, said polymeric covering softens and said forming member self-forms to said second form and said forming member maintains said second form upon cooling.

2. The catheter section of claim 1 wherein the tubular forming member is selected from the group consisting of braids and coils.

3. The catheter section of claim 2 wherein the forming member comprises a member of the group consisting of metals and polymers.

4. The catheter section of claim 3 wherein the tubular forming member comprises a super-elastic alloy.

5. The catheter section of claim 1 wherein the tabular forming member comprises a super-elastic nickel-titanium alloy.

6. The catheter section of claim 5, wherein the super-elastic alloy has a transition temperature below 25° C.

7. The catheter section of claim 6, wherein the transition temperature is below 0° C.

8. The catheter section of claim 1, wherein the polymeric covering comprises a polyurethane.

9. The catheter section of claim 8, further comprising an inner passageway covered by an inner lubricious layer of a fluorocarbon polymer.

10. The catheter section of claim 1, further comprising an inner passageway covered by an inner lubricious layer.

11. The catheter section of claim 1, wherein said first shape is straight.

12. The catheter section of claim 1, wherein said second shape is S-shaped.

13. The catheter section of claim 1, wherein the second shape is a 45° bend.

14. The catheter section of claim 1, wherein the second shape is a 90° bend.

15. The catheter section of claim 1, wherein the polymeric covering comprises a polymer having a $T_g^o$ which is greater than the softening temperature.

16. The catheter section of claim 1, wherein the polymeric covering comprises a polymer having a $T_g^o$ less than the softening point of said polymer.

17. The catheter section of claim 1, wherein the polymeric covering comprises a layer of polyurethane and a layer of polyethylene.

* * * * *